US009824185B2

(12) United States Patent
Douglass et al.

(10) Patent No.: US 9,824,185 B2
(45) Date of Patent: Nov. 21, 2017

(54) ELECTRONIC HEALTH RECORDS DATA MANAGEMENT SYSTEMS AND METHODS

(71) Applicant: PRACTICE FUSION, INC., San Francisco, CA (US)

(72) Inventors: Matthew Christopher Douglass, San Francisco, CA (US); Jonathan Mark Malek, Sacramento, CA (US)

(73) Assignee: Practice Fusion, Inc., San Francisco, CA (US)

( * ) Notice: Subject to any disclaimer, the term of this patent is extended or adjusted under 35 U.S.C. 154(b) by 434 days.

(21) Appl. No.: 14/455,091

(22) Filed: Aug. 8, 2014

(65) Prior Publication Data

US 2016/0042124 A1 Feb. 11, 2016

(51) Int. Cl.
*G06F 17/00* (2006.01)
*G06F 19/00* (2011.01)
*G06F 17/30* (2006.01)

(52) U.S. Cl.
CPC ...... *G06F 19/322* (2013.01); *G06F 17/30011* (2013.01)

(58) Field of Classification Search
CPC .................. G06F 17/30011; G06F 19/322
USPC .......................................... 707/607
See application file for complete search history.

(56) References Cited

U.S. PATENT DOCUMENTS

| | | | | |
|---|---|---|---|---|
| 6,551,243 | B2* | 4/2003 | Bocionek | A61B 5/411 128/923 |
| 7,523,118 | B2* | 4/2009 | Friedlander | G06F 17/30592 |
| 7,647,320 | B2* | 1/2010 | Mok | G06Q 50/22 705/2 |
| 7,756,728 | B2* | 7/2010 | Maughan | G06F 19/322 705/2 |
| 8,000,977 | B2* | 8/2011 | Achan | G06Q 10/103 705/2 |

(Continued)

OTHER PUBLICATIONS

Bahga, Arshdeep, et al., "A Cloud-based Approach for Interoperable Electronic Health Records (EHRs)", IEEE Journal of Biomedical and Health Informatics, vol. 17, No. 5, Sep. 2013, pp. 894-906.*

(Continued)

*Primary Examiner* — Robert Stevens
(74) *Attorney, Agent, or Firm* — Sterne, Kessler, Goldstein & Fox P.L.L.C.

(57) ABSTRACT

Systems and methods are disclosed for managing and storing electronic health records data. In an embodiment, a database module containing a plurality of databases stores a plurality of different types of patient medical data records. Each patient medical data record is composed of one or more categories of data which may be stored in different databases. A server module configured to respond to requests received from a client is connected to the database module. The server module includes a layer of application logic, a layer of composite services, a layer of domain services, and a layer of foundation services. A request received by the server module is first processed by the application logic, then by the appropriate composite services, domain services and foundation services. Domain services may communicate with the database module, generating a response that may be processed by the composite and application logic layers before sending back to the client.

17 Claims, 4 Drawing Sheets

(56) References Cited

U.S. PATENT DOCUMENTS

| | | | | |
|---|---|---|---|---|
| 8,606,593 B1* | 12/2013 | Green, III | | G06Q 10/06 |
| | | | | 705/2 |
| 2002/0007284 A1* | 1/2002 | Schurenberg | | G06Q 10/10 |
| | | | | 705/2 |
| 2002/0178031 A1* | 11/2002 | Sorensen | | G06Q 50/22 |
| | | | | 705/2 |
| 2004/0122707 A1* | 6/2004 | Sabol | | G06F 19/322 |
| | | | | 705/2 |
| 2006/0136270 A1* | 6/2006 | Morgan | | G06F 17/2264 |
| | | | | 705/3 |
| 2007/0203754 A1* | 8/2007 | Harrington | | G06F 19/322 |
| | | | | 705/3 |
| 2008/0046292 A1* | 2/2008 | Myers | | G06F 17/30557 |
| | | | | 705/3 |
| 2010/0082369 A1* | 4/2010 | Prenelus | | G06F 19/322 |
| | | | | 705/3 |
| 2011/0010195 A1* | 1/2011 | Cohn | | G06Q 50/24 |
| | | | | 705/3 |
| 2011/0202370 A1* | 8/2011 | Green, III | | G06F 19/328 |
| | | | | 705/3 |
| 2011/0246224 A1* | 10/2011 | Green, III | | G06Q 10/06 |
| | | | | 705/2 |
| 2012/0059668 A1* | 3/2012 | Baldock | | G06Q 10/10 |
| | | | | 705/3 |
| 2012/0166226 A1* | 6/2012 | Lee | | G06Q 10/10 |
| | | | | 705/3 |
| 2012/0191716 A1* | 7/2012 | Omoigui | | H01L 27/1463 |
| | | | | 707/740 |
| 2012/0253848 A1* | 10/2012 | Gazula | | G06Q 50/22 |
| | | | | 705/3 |
| 2014/0108048 A1* | 4/2014 | Cohn | | G06Q 50/24 |
| | | | | 705/3 |
| 2014/0316813 A1* | 10/2014 | Bauer | | G06F 19/3487 |
| | | | | 705/3 |
| 2015/0242571 A1* | 8/2015 | Naeymi-Rad | | G06F 19/322 |
| | | | | 705/3 |
| 2016/0063191 A1* | 3/2016 | Vesto | | G06F 17/30 |
| | | | | 705/2 |

OTHER PUBLICATIONS

Weber, Griffin M., et al., "The Shared Health Research Information Network (SHRINE): A Prototype Federated Query Tool for Clinical Data Repositories", J. Am. Med. Inform. Assoc., vol. 16, No. 5, © 2009, pp. 624-630.*

Allamaraju, Subrahmanyam, et al., Professional Java E-Commerce, Wrox Press Ltd, Birmingham, UK, Feb. 2001, pp. 71-94.*

Microsoft Computer Dictionary, 4th Edition, Microsoft Press, Redmond, WA, © 1999, pp. 123, 183 and 295-296.*

Wu, Ruoyu, et al., "Secure Sharing of Electronic Health Records in Clouds", 8th International Conf. on Collaborative Computing: Networking, Applications and Worksharing, Collaboratecom 2012, Pittsburgh, PA, Oct. 14-17, 2012, pp. 711-718.*

* cited by examiner

ELECTRONIC HEALTH RECORDS DATA MANAGEMENT SYSTEMS AND METHODS

BACKGROUND

Field

This field is generally related to managing and storing electronic health records.

Background

Electronic Health Records

Medical records related to a patient's health information are essential to the practice of medical care. Traditionally, medical records were paper-based documents. The emergence of electronic medical records (EMR), which are digital version of the paper chart that contains all of a patient's medical history from one medical practice, offers medical professionals and patients with new functionalities and efficiencies that paper-based medical records cannot provide. An electronic health record (EHR), also known as an electronic medical record (EMR), is a collection of electronically stored information about an individual patient's medical history. EHRs may contain a broad range of data, including demographics, medical history, medication history, allergies, immunization records, laboratory test results, radiology images, vital signs, personal statistics like age and weight, and billing information. Many commercial EHR systems combine data from a number of healthcare services and providers, such as clinical care facilities, laboratories, radiology centers, and pharmacies.

EHRs are a drastic improvement over paper-based medical records. Paper-based medical records require a large amount of physical storage space. Paper records are often stored in different locations, and different medical professionals may each have different and incomplete records about the same patient. Obtaining paper records from multiple locations for review by a healthcare provider can be time consuming, complicated, and sometimes impossible. In contrast, EHR data is stored in digital format, and thus are more secure and can be accessed from anywhere. EHR systems significantly simplify the reviewing process for healthcare providers. Because records in EHRs can be linked together, EHRs vastly improve the accessibility of health records and the coordination of medical care.

EHRs also decrease the risk of misreading errors by healthcare professionals. Poor legibility is often associated with handwritten, paper medical records, which can lead to medical errors. EHRs, on the other hand, are inherently legible given that they are typically stored in typeface. In addition, EHRs enhance the standardization of forms, terminology and abbreviations, and data input, which help ensure reliability of medical records, and standardization of codesets and storage of EHR data means that data from different technical information systems can be displayed in a single, unified record. Further, EHRs can be transferred electronically, thus reducing delays and errors in recording prescriptions of communicating laboratory test results.

The benefits of digitizing health records are substantial. Healthcare providers with EHR systems have reported better outcomes, fewer complications, lower costs, and fewer malpractice claim payments. But despite EHRs' potential in drastically improving the quality of medical care, only a low percentage of healthcare providers use EHR systems. While the advantages of EHRs are significant, they also carry concerns, including high costs, lost productivity during EHR implementation or computer downtime, and lack of EHR usability.

The Health Insurance Portability and Accountability Act (HIPAA), enacted in the U.S. in 1996, and as amended, established rules for use and access of protected health information (PHI). HIPAA provides restrictions on disclosure of and access to protected health information to and by third parties. HIPAA applies to information in electronic medical records, such as health information doctors and nurses input, documented conversations between a doctor and a patient, and information use to process or facilitate medical billing claims and documents. The HIPAA Security Rule, effective on Apr. 20, 2005 for most covered entities, adds additional constraints to electronic data security and the storage and transmission of PHI.

The high cost of EHR systems also significantly hinders EHR adoption. A large number of physicians without EHR systems have referred to initial capital costs as a barrier to adopting EHR systems. Cost concerns are even more severe in smaller healthcare settings, because current EHR systems are more likely to provide cost savings for large integrated institutions than for small physician offices. During the EHR system technology's setup and implementation process, productivity loss can further offset efficiency gains. The need to increase the size of information technology staff to maintain the system adds even more costs to EHR system usages.

Usability is another major factor that holds back adoption of EHR systems. It is particularly challenging to develop user-friendly EHR systems. There is a wide range of data that needs to be integrated and connected. Complex information and analysis needs vary from setting to setting, among healthcare provider groups, and from function to function within a healthcare provider group. To some providers, using electronic medical records can be tedious and time consuming, and the complexity of some EHR systems renders the EHR usage less helpful. Some doctors and nurses also complain about the difficulty and the length of time to enter patients' health information into the system.

Under-utilization of EHR systems, despite incentives and mandates from the government and the tremendous potential of EHR systems in revolutionizing the healthcare system, calls for better EHR systems that are secure, cost-effective, efficient, and user-friendly.

Comprehensive EHR systems can provide capabilities far beyond simply storing patients' medical records. Because EHR systems offer healthcare providers and their workforce members the ability to securely store and utilize structured health information, EHR systems can have a profound impact on the quality of the healthcare system. In Framework for Strategic Action on Health Information Technology, published on Jul. 21, 2004, the Department of Health & Human Services (HHS) outlined many purposes for EHR services. The outlined purposes include, among other things, improving healthcare outcomes and reducing costs, reducing recordkeeping and duplication burdens, improving resource utilization, care coordination, active quality and health status monitoring, reducing treatment variability, and promoting patients' engagement in and ownership over their own healthcare.

Recent legislation has set goals and committed significant resources for health information technology (IT). One of the many initiatives of the American Recovery and Reinvestment Act of 2009 (ARRA) was "to increase economic efficiency by spurring technological advances in science and health." The Health Information Technology for Economic and Clinical Health (HITECH) Act, passed as a part of ARRA, allocated billions of dollars for healthcare providers to adopt and meaningfully use EHR systems in their practices. HITECH also mandates the Office of the National Coordinator for Health information Technology (ONC) to define certification criteria for "Certified EHR Technology."

EHR systems satisfying "Certified EHR Technology" criteria are capable of performing a wide range of functions, including: entry and storage, transmission and receipt of care summaries, clinical decision support, patient lists and education resources, generation of public health submission data, and patient engagement tools. Entry and storage is related to the ability to enter, access and modify patient demographic information, vital signs, smoking status, medications, clinical and radiology laboratory orders and results. Transmission and receipt of care summaries involve the ability to receive, incorporate, display and transmit transition of care/referral summaries. Clinical decision support features configurable clinical decision support tools, including evidence-based support interventions, linked referential clinical decision support, and drug-drug and drug-allergy interaction checks. Patient lists and education resources include the ability to create patient lists based on problems, medications, medication allergies, demographics and laboratory test result values, and the ability to identify patient-specific education resources based on such data elements. Generating public health submission data allows users to create electronic immunization and syndromic surveillance data files that can be submitted to public health agencies. Patient engagement tools allow medical professionals to grant patients with an online means to view, download and transmit their health information to a third party, provide patients with clinical summaries after office visits, and facilitate secure-doctor patient messaging.

BRIEF SUMMARY

Systems and methods are disclosed for managing and storing electronic health records data. In an embodiment, a database module containing a plurality of databases stores a plurality of different types of patient medical data records. Each patient medical data record is composed of one or more categories of data which may be stored in different databases. A server module configured to respond to requests received from a client is connected to the database module. The server module includes a layer of application logic, a layer of composite services, a layer of domain services, and a layer of foundation services. A request received by the server module is first processed by the application logic, then by the appropriate composite services, domain services and foundation services. Domain services may communicate with the database module, generating a response that may be processed by the composite and application logic layers before sending back to the client.

Further embodiments, features, and advantages of the invention, as well as the structure and operation of the various embodiments, are described in detail below with reference to accompanying drawings.

BRIEF DESCRIPTION OF THE DRAWINGS

The accompanying drawings, which are incorporated herein and form part of the specification, illustrate the present disclosure and, together with the description, further serve to explain the principles of the disclosure and to enable a person skilled in the relevant art to make and use the disclosure.

The drawing in which an element first appears is typically indicated by the leftmost digit or digits in the corresponding reference number. In the drawings, like reference numbers may indicate identical or functionally similar elements.

DETAILED DESCRIPTION

Overview

Traditional EHR systems typically contain medical data related to a specific practice or institution. In many cases, each healthcare institution requires its own dedicated servers, database instances, and maintenance. Additionally, each system is commonly isolated from EHR system implementations of other institutions, complicating the process of sharing and collaboration among different healthcare providers.

A central, cloud-based EHR system can improve the process of sharing and collaboration by managing and storing medical data across all healthcare providers within a single system. By storing all medical data related to a patient in one system, the patient's complete history of care can easily be viewed and shared. Teams of healthcare providers are able to collaborate on a patient's health without the need to manually share files by facsimile, electronic mail, or other inconvenient means.

The amount of data stored in a cloud-based system as discussed above is normally much greater than that of a traditional EHR system, and the architecture of the system must address this concern. Many traditional EHR systems employ a single database architecture to store all medical data. This architecture generally has decreasing returns to scale as hardware improvements to match data growth can be costly. Additionally, without significant hardware improvements, search performance decreases as the average size of each database table and index increases. This can cause standard read and write operations to become less efficient.

Embodiments of the present invention employ a layered, services-oriented server architecture alongside a database system containing a plurality of databases. The distribution of data throughout the plurality of databases allows for cost efficient, horizontal scaling as the amount of data grows. In an embodiment, the database system is partitioned based on categories of data (e.g. patients, practices, lab results) and distributed throughout the plurality of databases. These server and database architectures allow for improved code modularity and code reuse. As a result, system component testing and updates are simplified.

In the detailed description that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

System

Figure 1:
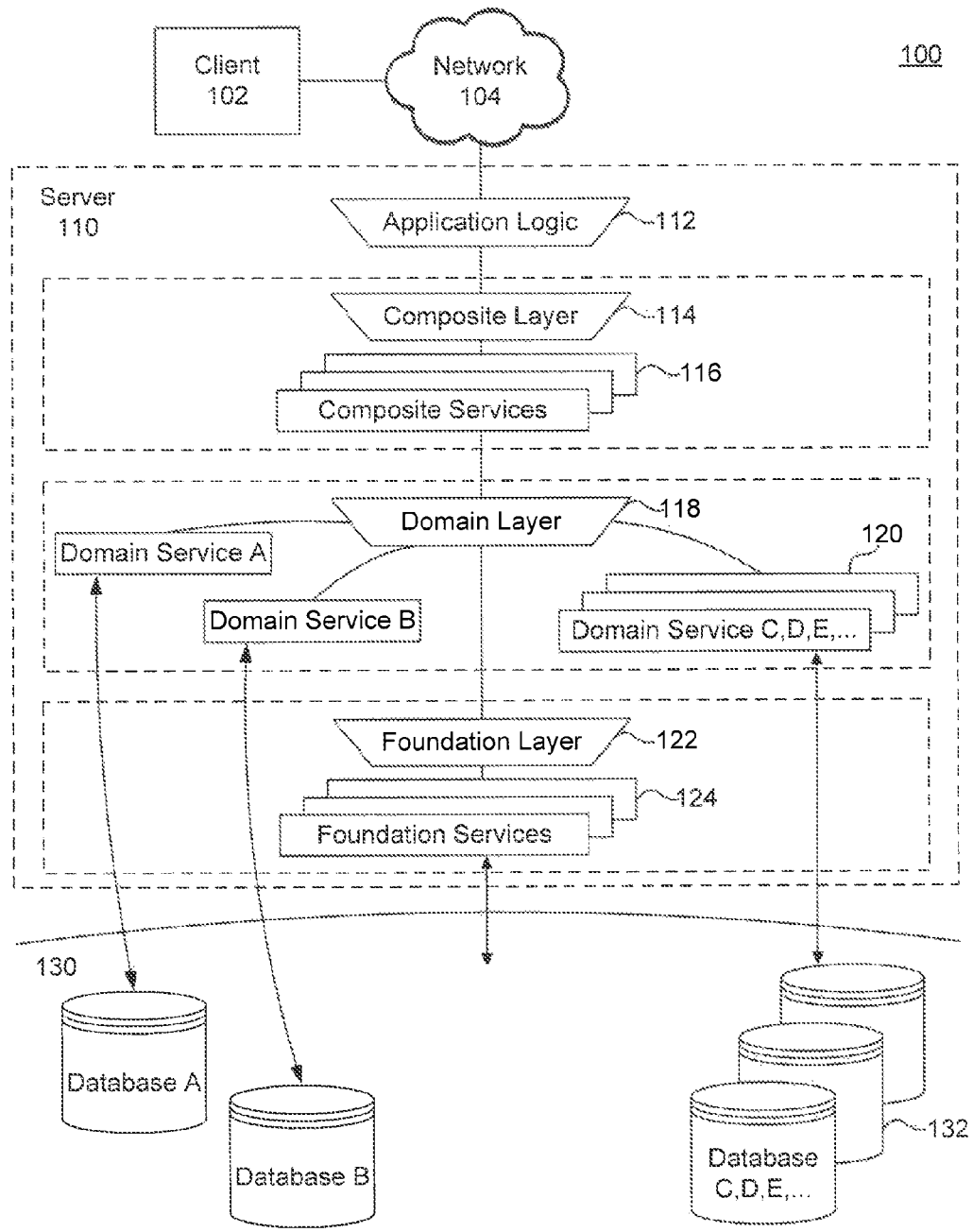
FIG. 1 is a diagram illustrating an example system for managing and storing electronic health records data, according to an embodiment.

FIG. 1 is a diagram illustrating an example system for managing and storing electronic health records data, according to an embodiment.

In the embodiment of FIG. 1, the central EHR system 100 includes a server 110 and a database system 130. The server 110 is configured to receive and respond to requests sent from a client 102 via a network 104, such as the Internet. Client 102 may, for example, include a web browser that enables a user to interact with the EHR system. The web browser can respond to user input by sending an HTTP request to server 110 via network 104. In another example, the user may interface with client 102 through a native application instead of a web browser, such that the native application communicates with server 110. Client 102 may be any type of computing device, such as and without limitation, a PC, laptop, or mobile device.

Database system 139 includes a plurality of databases 132 storing a plurality of different types of patient medical data records. Each patient medical data record includes one or more categories of data and may reference additional categories. For example, a data record representing a laboratory result may contain data about the actual test results, and contain references to data about the specified patient and the practice that requested the laboratory test. Such references may be, for example, pointers to the referenced data in other databases. In an embodiment, the database system 130 is partitioned by categories of data (e.g. patients, practices, lab results). The different categories are then distributed throughout the plurality of databases. In one example embodiment, the data is distributed such that each category of data resides in a single database. In another example embodiment, the data is distributed such that only One category of data resides in each database.

Server 110 is connected to database system 130. In an embodiment, server 110 is connected to database system 130 via a network, such as the Internet or a local area network (LAN). In another embodiment, server 110 and database system 130 are implemented on the same computing system and/or device. Server 110 includes an application logic layer 112, a composite layer 114, a domain layer 118 and a foundation layer 122. Domain layer 118 includes a plurality of domain services 120 that are typically responsible for interacting with database system 130. Each domain service is self-contained and may be called while processing different requests received by server 110. Each domain service corresponds to a category of data stored in database system 130. For example, one domain service may be responsible for all patient data, another for practice data, and another for lab results data. In an embodiment where only one category of data resides in each database and each category of data resides in a single database, as illustrated in FIG. 1, a one to one mapping exists between domain services 120 and plurality of databases 132. Domain services 120 may issue create, read, update and delete (CRUD) operations to database system 130. While interactions commonly occur between domain layer 118 and database system 130 during normal workflow, foundation layer 122, composite layer 114, and application logic layer 112 may also interact directly with database system 130 when appropriate.

Composite layer 114 includes a plurality of composite services 116. Each composite service is self-contained and may be called while processing different requests received by server 110. Composite services 116 may make calls to domain services 120 to read from and write to database system 130. Composite services 116 may also interact with database system 130 directly. Each composite service may make calls to multiple domain services and is responsible for integrating the response data from each called domain service. One example of a composite service, in an embodiment, is an authorization service. For each request that is received by server 110, the first action may be to call the authorization service to ensure the requester has appropriate permissions to make the request. The authorization service may call multiple domain services to gather the appropriate information, integrate and evaluate that information, and return a response to the service's caller.

Application logic layer 112 serves as an application endpoint, configured to receive requests from client 102 via network 104. In the embodiment of FIG. 1, application logic layer 112 is configured to make calls to composite layer 114 and domain layer 118 in the process of servicing a request. Application logic layer 112 contains preprogrammed logic for actions to be taken when a request is received. For instance, a request may be received to retrieve all history of a patient. In this case, application logic layer 112 receives the request and contains logic to retrieve the appropriate data from database system 130. Application logic layer 112 retrieves the appropriate data by calling specific composite services in composite layer 114 and domain services in domain layer 118. When responses are received from these service calls, the application logic layer integrates the response data and formulates a response to be communicated back to client 102.

Foundation layer 122 includes a plurality of foundation services 124. Each foundation service is self-contained and may be called while processing different requests received by server 110. The foundation layer primarily acts as a utility layer that performs actions across multiple collections of data. For example, the foundation layer may include an auditing service that tracks all create, read, update, and delete operations with respect to database system 130. The foundation layer may also include a logging service that records log messages for events that occur within the other layers of server 110. Both of these example services act on the system as a whole, and foundation services may be invoked from any of application logic layer 112, composite layer 114, and domain layer 118. In an embodiment, foundation services 124 may interact directly with database system 130. In other embodiments, foundation services 124 may interact with other structured data stores distinct from database system 130.

Server 110 may be implemented on computing devices having server functionality, in hardware, software, or any combination thereof. Such computing devices can include, but are not limited to, a personal computer, a mobile device such as a mobile phone, workstation, embedded system, game console, television, set-top box, or any other computing device. Further, a computing device can include, but is not limited to, a device having a processor and memory, including a nontransitory memory, for executing and storing instructions. The memory may tangibly embody the data and program instructions. Software may include one or more applications and an operating system. Hardware can include, but is not limited to, a processor, memory, and graphical user interface display. The computing device may also have multiple processors and multiple shared or separate memory components. For example, the computing device may be a part of or the entirety of a clustered computing environment or server farm.

The layered and partitioned architecture of the system as described above simplifies the development and testing of individual system components. For example, in the embodiment of FIG. 1, the laboratory results component of the system can be updated without affecting the rest of the system. The domain service and database related to laboratory results may be taken offline to manage system changes while the rest of the system remains online and functional. Similarly, component testing is simplified by limiting the code and number of system states that need to be tested. Since each service is independent and its logic is encapsulated from the rest of the system, the service can straightforwardly be tested from both a black-box and white-box perspective. Full component tests are easy to target with high level calls to the appropriate services. System security also becomes simpler to manage with dedicated authorization and validation services.

Figure 2:
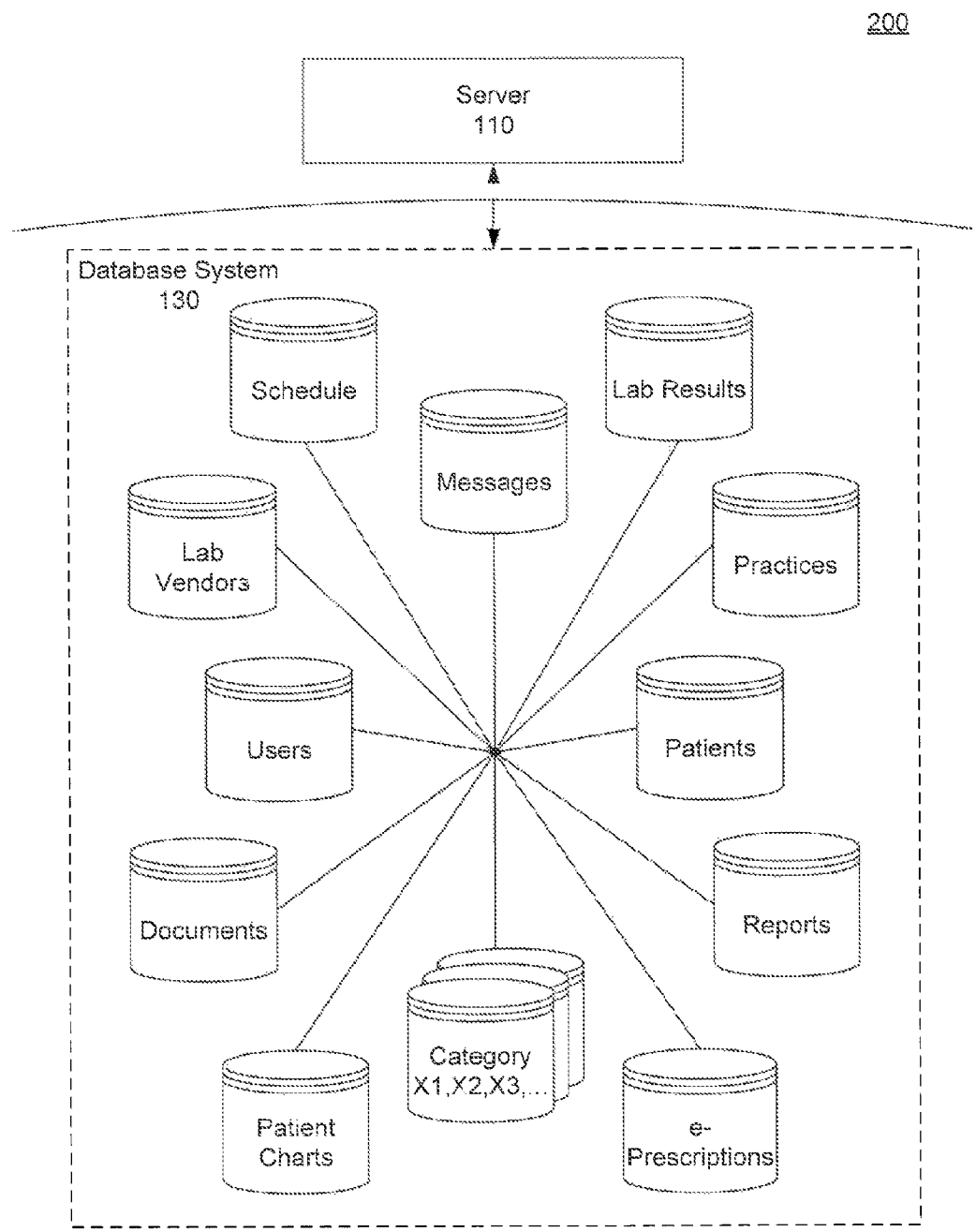
FIG. 2 is a diagram illustrating an example database system for managing and storing electronic health records data partitioned by categories of data, according to an embodiment.

FIG. 2 is a diagram illustrating an example database system 130 for managing and storing electronic health records data partitioned by categories of data, according to an embodiment.

In the embodiment of FIG. 2, the medical data stored in database system 130 is partitioned based on, for example but not limited to, the following categories: practice data, patient data, message data, schedule data, document data, patient chart data, lab vendor data, lab results data, report data, user data and e-prescription data. In other embodiments, the medical data may also be partitioned based on one or more of additional categories X1, X2, X3, . . . , as illustrated in FIG. 2, and/or one or more of the previously stated categories. Categories X1, X2, X3, . . . may denote any logical category of medical-related data. In the illustrated embodiment, each category of data resides in its own database. Database system 130 may be distributed in that the plurality of databases reside on different computing devices or in different locations. Conversely, the plurality of databases in database system 130 may reside in the same physical location or on the same computing device.

Each category of data stored in the database corresponds to a domain service implemented on server 110. In the embodiment of FIG. 2, each database has its own corresponding domain service as each database contains exactly one category of data. One of skill in the art will recognize, though, that a single category of data can also be split across multiple databases. As described above with respect to FIG. 1, this database architecture allows for simplified change management and testing. When an update to a database is needed, such as but not limited to a schema update, the database can be temporarily taken offline without affecting the rest of the system. Testing of system components also need only take into account the databases in which relevant data resides.

Additionally, by partitioning database system 130 into categories of data, in an embodiment, data for all users can be stored in each database. For example, in the embodiment of FIG. 2, message data for all users is stored in a single database. This architecture can improve the efficiency of queries related to multiple users. In the instance of message data, a request to retrieve all messages for a particular practice will be made considerably more efficient by retrieving data from only a single database.

Figure 3:
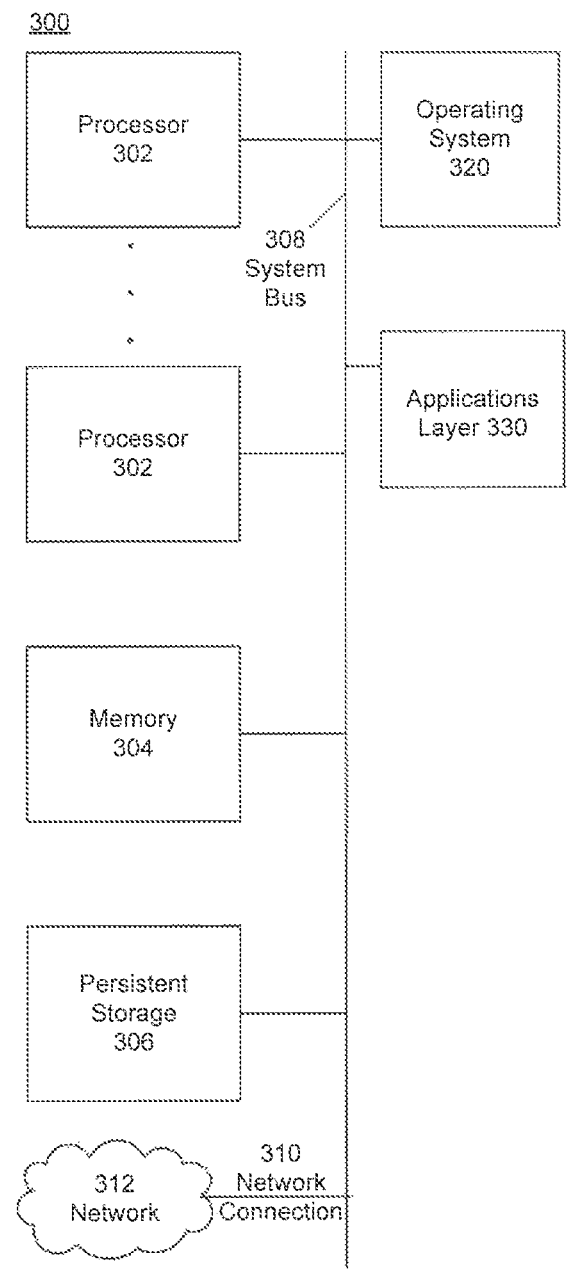
FIG. 3 is a diagram illustrating an example computing device, according to an embodiment.

FIG. 3 is a diagram illustrating an example computing device, according to an embodiment. A computing device 300 accesses a network 312 over a network connection 310 that provides computing device 300 with telecommunications capabilities. Computing device 300 uses an operating system 320 as software that manages hardware resources and coordinates the interface between hardware and software.

In an embodiment, computing device 300 contains a combination of hardware, software, and firmware constituent parts that allow it to run an applications layer 330. Computing device 300, in embodiments, may be organized around a system bus 308, but any type of infrastructure that allows the hardware infrastructure elements of computing device 300 to communicate with and interact with each other may also be used.

Processing tasks in the embodiment of FIG. 3 are carried out by one or more processors 302. However, it should be noted that various types of processing technology may be used here, including multi-core processors, multiple processors, or distributed processors. Additional specialized processing resources such as graphics, multimedia, or mathematical processing capabilities may also be used to aid in certain processing tasks. These processing resources may be hardware, software, or an appropriate combination thereof. For example, one or more of processors 302 may be a graphics-processing, unit (GPU). In an embodiment, a GPU is a processor that is a specialized electronic circuit designed to rapidly process mathematically intensive applications on electronic devices. The CPU may have a highly parallel structure that is efficient for parallel processing of large blocks of data, such as mathematically intensive data common to computer graphics applications, images and videos.

In order to manipulate data in accordance with embodiments described herein, processors 302 access a memory 304 via system bus 308. Memory 304 is nontransitory memory, such as random access memory (RAM). Memory 304 may include one or more levels of cache. Memory 304 has stored therein control logic (i.e., computer software) and/or data. For data that needs to be stored more permanently, processors 302 access persistent storage 306 via system bus 308. Persistent storage 306 may include, for example, a hard disk drive and/or a removable storage device or drive. A removable storage drive may be an optical storage device, a compact disc drive, flash memory, a floppy disk drive, a magnetic tape drive, tape backup device, and/or any other storage device/drive.

Processors 302, memory 304, and persistent storage 306 cooperate with operating system 320 to provide basic functionality for computing device 300. Operating system 320 provides support functionality for applications layer 330.

Network connection 310 enables computing device 300 to communicate and interact with any combination of remote devices, remote networks, remote entities, etc. For example, network connection 310 may allow computing device 300 to communicate with remote devices over network 312, which may be a wired and/or wireless network, and which may include any combination of LANs, WANs, the Internet, etc. Control logic and/or data may be transmitted to and from computer device 300 via network connection 310.

Applications layer 330 may house various modules, components and services. For example, application logic 112, composite services 116, domain services 120, and foundation services 124 may be included in applications layer 330 when computing device 300 is used as server 110.

It should be noted that computer-readable medium embodiments may include any physical medium which is capable of encoding instructions that may subsequently by used by a processor to implement methods described herein. Example physical media may include floppy discs, optical discs (e.g. CDs, mini-CDs, DVDs, HD-DVD, Blu-ray), hard drives, punch cards, tape drives, flash memory, or memory chips. However, any other type of tangible, persistent storage that can serve in the role of providing instructions to a processor may be used to store the instructions in these embodiments.

Method

Figure 4:
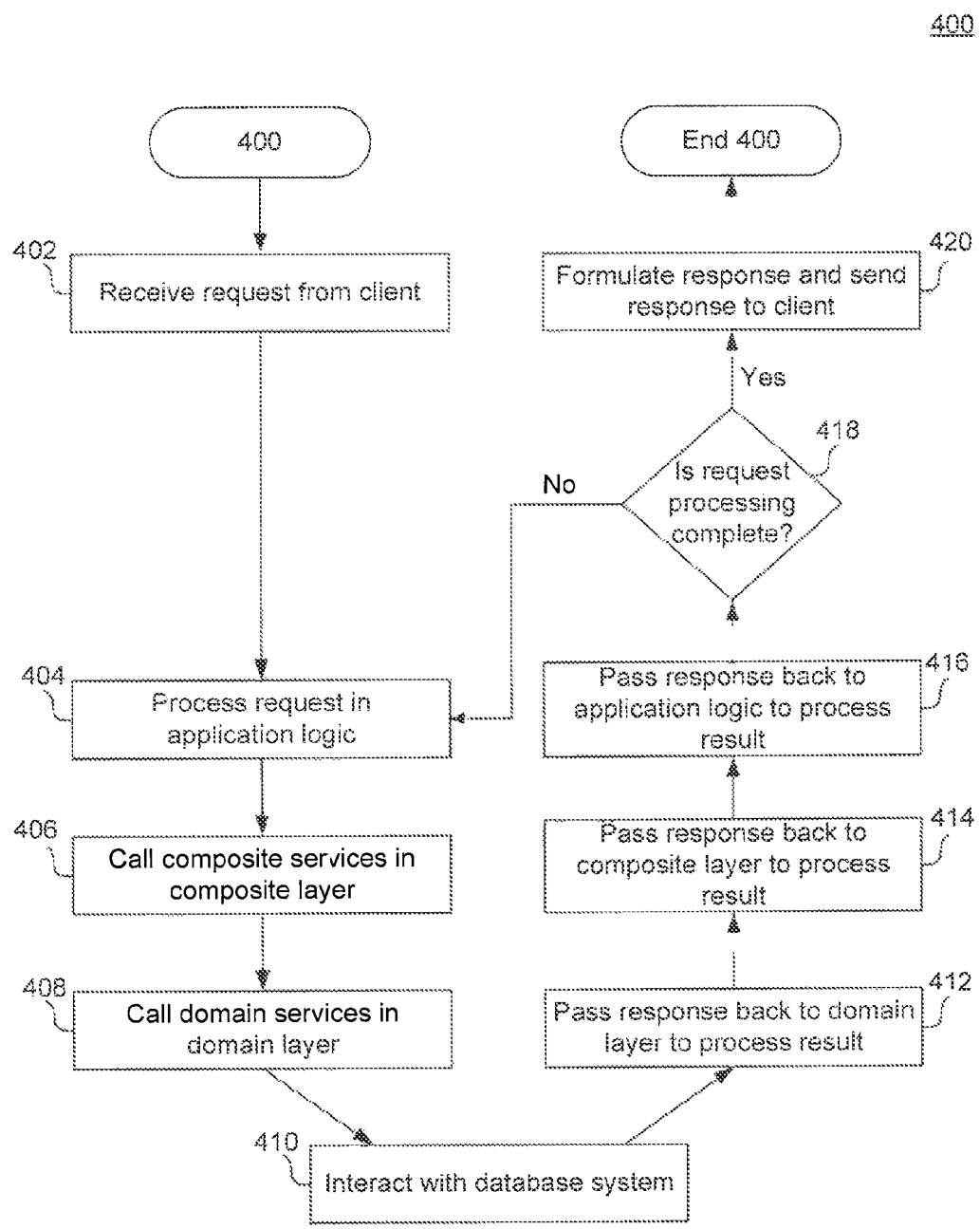
FIG. 4 is a flowchart illustrating an example method for receiving and processing a request from a client.

FIG. 4 is a flowchart illustrating an example method for receiving and processing a request from a client.

Method 400 begins at step 402 by receiving a request from a client via a network, such as the Internet. In an embodiment, the request is received by a central EHR system as described with respect to FIG. 1. For example, a request may be received to retrieve a patient's history of care for the past year. For purposes of explanation, this example request will be referenced in the description of each step. The application logic layer of the system may be the application endpoint that receives the request. At step 404, preprogrammed application logic processes the request and determines the actions that need to be taken to complete the request, including composite services and domain services that must be called.

At step 406, one or more composite services in the composite layer are called. At step 408, one or more domain services in the domain layer are called. An authorization composite service may be called first to ensure the request has sufficient permissions to complete. With respect to the example request, the authorization service checks that the requester is authorized to view the history of care for a particular patient. To determine Whether the request has sufficient permissions to complete, the authorization service may call one or more domain services.

The domain services called at step 408 interact with a database system at step 410 to gather the appropriate data. This database system may be similar to, for example, that described with respect to FIGS. 1 and 2. The gathered data is returned to the domain services in responses from the database system at step 412. In an embodiment, the domain services may issue create, read, update, and delete (CRUD) operations to the database system when servicing a request received by the EHR system. The domain services return responses containing the gathered data from the database system to the appropriate composite service at step 414 (such as the authorization composite service in the example provided above). When called directly from the application logic, domain services may return responses containing the gathered data to the application logic at step 416.

The gathered data for each composite service is integrated and processed at step 414, and a response is returned to the application logic layer at step 416. In the authorization example above, the response indicates whether the request has sufficient permissions to complete. This response is processed at step 416 to identify further actions to take when servicing the received request.

At step 418, a check is performed to determine whether request processing is complete. If there are no further actions to take, a final response is formulated at step 420 and sent to the client. Continuing the same example, if the authorization service determines that the request does not have sufficient permissions to complete, a response indicating that the user is not authorized to make this request may be sent to the client.

Returning to step 418, if there are still further actions to take when servicing the request, the application logic further processes the request at step 404 and issues calls to the appropriate composite and domain services at steps 406 and 408, respectively. With respect to the example request, if the authorization service determines that the request has sufficient permissions to complete, request processing continues by gathering data related to the patient's history of care for the past year.

As data is gathered at step 410, responses are again returned to the appropriate domain services at step 412. Domain services process the responses and in turn send responses to the appropriate composite services at step 414 or application logic at step 416. Composite services receiving responses at step 414 further process and integrate the returned data and send a new response to the application logic at step 416. At step 418, a cheek is once again performed to determine whether request processing is complete.

Once all necessary data has been gathered, a response containing the data is formulated and sent to the client at step 420 via a network, such as the Internet. The response may be formulated to provide a useful representation of the data to the client. For example, the data may first be sorted before sending the response to the client.

CONCLUSION

Identifiers, such as "(a)," "(b)," "(i)," "(ii)," etc., are sometimes used for different elements or steps. These identifiers are used for clarity and do not necessarily designate an order for the elements or steps.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An electronic health records (EHR) system, comprising:
    a medical database system comprising a plurality of databases storing different types of patient medical data records, each patient medical data record comprising one or more categories of data and a reference to data stored in other databases of the medical database system, and wherein each of the plurality of databases stores one or more categories of data such that no category of data resides in more than one database; and
    a server coupled to the medical database system, the server comprising at least one processor coupled to a memory and configured to:

receive a request for medical data related to a patient at a central EHR system via a network from a requester;

process the request to determine one or more categories of data corresponding to the requested medical data;

identify a composite service within the server associated with at least one of the determined categories of data, wherein the composite service is self-contained and executes independently from other composite services;

execute the composite service within the server to identify a domain service within the server corresponding to one of the determined categories of data, wherein the domain service is self-contained and executes independently from other domain services;

execute the domain service within the server to identify a database within a medical database system, wherein the identified database stores patient medical data records comprising the category of data corresponding to the domain service;

query, by the identified domain service within the server, the identified database to retrieve a patient medical data record matching the requested medical data;

integrating, by the composite service within the server, the retrieved patient medical data record into an aggregated response; and sending, by an application logic layer within the server, the aggregated response via the network to the requester.

2. The system of claim 1, the at least one processor further configured to:

execute a plurality of foundation services within the server configured to perform utility functions and configured to interact with the plurality of databases of the medical database system, wherein execution of the plurality of foundation services can be initiated by the domain service, the composite service, and the application logic layer.

3. The system of claim 1, wherein the server is coupled to the medical database system via a network.

4. The system of claim 1, wherein the plurality of databases of the medical database system are located in the same physical location.

5. The system of claim 1, wherein the categories of data stored in the plurality of databases of the medical database system comprise: practice data, patient data, message data, schedule data, document data, patient chart data, lab vendor data, lab results data, report data and e-prescription data.

6. The system of claim 1, wherein the composite service is an authorization service configured to determine whether the request received by the server has sufficient permissions to complete.

7. An electronic health records (EHR) system, comprising:

a medical database system comprising a plurality of databases storing different types of patient medical data records, each patient medical data record comprising one category of data and a reference to data stored in other databases of the medical database system, and wherein each of the plurality of databases stores at most one category of data; and a server coupled to the medical database system, the server comprising at least one processor coupled to a memory and configured to:

receive a request for medical data related to a patient at a central EHR system via a network from a requester;

process the request to determine one or more categories of data corresponding to the requested medical data;

identify a composite service within the server associated with at least one of the determined categories of data, wherein the composite service is self-contained and executes independently from other composite services;

execute the composite within the server service to identify a domain service within the server corresponding to one of the determined categories of data, wherein the domain service is self-contained and executes independently from other domain services;

execute the domain service within the server to identify a database within a medical database system, wherein the identified database stores patient medical data records comprising the category of data corresponding to the domain service;

query, by the identified domain service within the server, the identified database to retrieve a patient medical data record matching the requested medical data;

integrating, by the composite service within the server, the retrieved patient medical data record into an aggregated response; and sending, by an application logic layer within the server, the aggregated response via the network to the requester.

8. The system of claim 7, the at least one processor further configured to:

execute a plurality of foundation services within the server configured to perform utility functions and configured to interact with the plurality of databases of the medical database system, wherein execution of the plurality of foundation services can be initiated by the domain service, the composite service, and the application logic layer.

9. The system of claim 7, wherein the server is coupled to the medical database system via a network.

10. The system of claim 7, wherein the plurality of databases of the medical database system are located in the same physical location.

11. The system of claim 7, wherein the categories of data stored in the plurality of databases of the medical database system comprise: practice data, patient data, message data, schedule data, document data, patient chart data, lab vendor data, lab results data, report data and e-prescription data.

12. The system of claim 7, wherein the composite service is an authorization service configured to determine whether the request received by the server has sufficient permissions to complete.

13. A computer-implemented method for managing and storing electronic health records (EHR) data, comprising:

receiving a request for medical data related to a patient at a central EHR system via a network from a requester;

processing the request to determine one or more categories of data corresponding to the requested medical data;

identifying a composite service associated with at least one of the determined categories of data, wherein the composite service is self-contained and executes independently from other composite services;

executing the composite service to identify a domain service corresponding to one of the determined categories of data, wherein the domain service is self-contained and executes independently from other domain services;

executing the domain service to identify a database within a medical database system, the medical database system comprising a plurality of databases storing different types of patient medical data records, wherein the identified database stores patient medical data records comprising the category of data corresponding to the domain service, and wherein the medical database system is part of the central EHR system;

querying, by the identified domain service, the identified database to retrieve a patient medical data record matching the requested medical data;

integrating, by the composite service, the retrieved patient medical data record into an aggregated response; and sending the aggregated response via the network to the requester.

14. The method of claim 13, wherein the querying the identified database is accomplished via a network.

15. The method of claim 13, wherein the plurality of databases of the medical database system are located in the same physical location.

16. The method of claim 13, wherein the plurality of patient medical data records stored in the medical database system each comprise one or more categories of data including: practice data, patient data, message data, schedule data, document data, patient chart data, lab vendor data, lab results data, report data and e-prescription data.

17. The method of claim 13, wherein the integrating further comprises combining the retrieved patient medical data record with other patient medical data records retrieved from different databases of the medical database system.

* * * * *